US00PP12689P2

(12) United States Plant Patent
Churchus

(10) Patent No.: US PP12,689 P2
(45) Date of Patent: Jun. 11, 2002

(54) SUTERA PLANT NAMED 'EVERWHITE'

(75) Inventor: John William Churchus, Devon Meadows (AU)

(73) Assignee: Plants Management Australia Pty. Ltd., Wonga Park (AU)

( * ) Notice: Subject to any disclaimer, the term of this patent is extended or adjusted under 35 U.S.C. 154(b) by 0 days.

(21) Appl. No.: 09/797,248

(22) Filed: Mar. 1, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Sutera plant named 'Everwhite', characterized by its cascading plant habit; rapid growth rate; freely branching habit; small dark green-colored leaves; large white-colored flowers; and continuous flowering habit.

1 Drawing Sheet

BACKGROUND OF THE INVENTION

The present Invention relates to a new and distinct cultivar of Sutera plant, botanically known as *Sutera cordata*, and hereinafter referred to by the name 'Everwhite'.

The new Sutera originated from a cross made by the Inventor in Devon Meadows, Victoria, Australia, of a proprietary Sutera seedling selection identified as JC 9604, not patented, as the female, or seed, parent with the Sutera cultivar Snowflake, not patented, as the male, or pollen, parent.

The new Sutera was discovered and selected by the Inventor as a flowering plant within the progeny of the stated cross in a controlled environment in Devon Meadows, Victoria, Australia in November, 1997. The selection of this plant was based on its growth habit and large white-colored flowers.

Asexual reproduction of the new cultivar by terminal cuttings taken at Devon Meadow, Victoria, Australia, since March, 1998, has shown that the unique features of this new Sutera are stable and reproduced true to type in successive generations.

SUMMARY OF THE INVENTION

Plants of the cultivar Everwhite have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Everwhite'. These characteristics in combination distinguish 'Everwhite' as a new and distinct cultivar:

1. Cascading plant habit.
2. Rapid growth rate.
3. Freely branching habit.
4. Small dark green-colored flowers.
5. Large white-colored flowers.
6. Continuous flowering habit.

In side-by-side comparisons conducted by the Inventor in Devon Meadows, Victoria, Australia, plants of the new Sutera have smaller leaves and larger flowers than plants of the female parent, the selection BJ 3; and plants of the new Sutera have much larger flowers and smaller leaves, more open growth habit, are faster-growing, and are more freely flowering than plants of the male parent, the cultivar Snowflake.

In side-by-side comparisons conducted by the Inventor in Devon Meadows, Victoria, Australia, plants of the new Sutera are more compact, have smaller and smoother leaves, have larger flowers, and flower more continuously than plants of the cultivar Blizzard, disclosed in U.S. Plant Pat. No. 10,966.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Sutera.

The photograph at the top of the sheet comprises a side perspective view of the new Sutera grown in a 25-cm hanging basket container.

The photograph at the bottom of the sheet comprises a close-up view of typical leaves and flowers of the new Sutera.

DETAILED BOTANICAL DESCRIPTION

In the following description, color references are made to The Royal Horticultural Society Colour Chart except where general terms of ordinary dictionary significance are used. Plants used for the description and the photographs were grown during the winter in 25-cm hanging basket containers in a polycarbonate-covered greenhouse and with cultural conditions which closely approximate commercial production conditions in Centerville, Ut. During the production of these plants, day temperatures averaged 25° C., night temperatures averaged 20° C., and light levels ranged from 2,500 to 4,000 foot-candles. Plants were about 16 weeks from planting rooted cuttings and were pinched about four weeks after planting.

Botanical classification: *Sutera cordata* cultivar Everwhite.
Parentage:

*Female, or seed, parent.*—Proprietary *Sutera cordata* seedling selection identified as code No. JC 9604, not patented.

*Male, of pollen, parent.*—*Sutera cordata* cultivar Snowflake, not patented.

Propagation:

*Type of cuttings.*—Terminal vegetative cuttings.

*Time to initiate roots, summer.*—About 8 days at 20° C.

*Time to initiate roots, winter.*—About 14 days at 18° C.

*Time to produce a rooted cutting, summer.*—About 28 days at 20° C.

*Time to produce a rooted cutting, winter.*—About 36 days at 18° C.

*Root description.*—Dense, fine, fibrous and freely-branching.

Plant description:

*Crop time.*—Rapid growth rate; from rooted liners, about 12 weeks are required to produce a fully-grown flowering plant in a 10-cm container and about 16 weeks are required to produce a fully-grown flowering plant in a 25-cm container. Strong and vigorous growth habit.

*Form.*—Mounded and cascading. Appropriate for 10-cm and larger containers.

*Total plant height.*—About 55 cm.

*Plant diameter or plant spread.*—About 120 cm.

*Branching habit.*—Freely branching; pinching enhances branching with lateral branches potentially forming at every node.

*Lateral branches.*—Length: About 55 cm. Diameter: About 1.5 mm. Internode length: About 4 mm. Texture: Smooth, glabrous. Color: Immature, 149A; mature, 147A.

*Foliage description.*—Leaves simple, generally symmetrical, opposite and long persisting. Quantity per lateral branch: About 30. Length: About 1 cm. Width: About 1 cm. Shape: Broadly ovate to rounded. Apex: Rounded. Base: Obtuse. Margin: Slightly dentate. Texture: Smooth, glabrous; leathery. Color: Young foliage, upper surface: 137A. Young foliage, lower surface: 138B. Mature foliage, upper surface: 137A; venation, 137A. Mature foliage, lower surface: 138B; venation, 138B. Petiole: Length: About 5 mm. Diameter: About 0.5 mm. Color: 137A.

Flower description:

*Flower type and habit.*—Solitary, axillary, salverform flowers; sympetalous; actinomorphic; slender corolla tube abruptly flared and five-lobed. Typically two flowers per node; flowering acropetally. Flowers face outward or droop. Flowers self-cleaning.

*Flower lastingness.*—Individual flowers last about two weeks on the plant.

*Natural flowering season.*—Continuously flowering from spring through fall, or year-round in the greenhouse with warm night temperatures, about 20° C.

*Quantity.*—Very freely flowering; more than 250 flower buds and open flowers per plant.

*Fragrance.*—None detected.

*Flower buds.*—Length: About 7.5 mm. Diameter: About 2 mm. Shape: Oblong, cylindrical. Color: 138A.

*Flower size.*—Diameter: About 1.5 cm. Height (depth): About 1.4 cm.

*Corolla.*—Petal quantity: Five, fused, non-imbricate. Petal lobe length (beyond tube): About 6 mm. Petal lobe width: About 3 mm. Petal shape: Oval. Petal apex: Rounded. Petal margin: Entire. Texture: Smooth. Color: Petal, upper surface, when opening and fully opened: More white than 155A. Petal, lower surface, when opening and fully opened: More white than 155A. Corolla throat: 12A to 12B. Corolla tube: More white than 155A.

*Calyx.*—Appearance: Narrow tube; sepals fused at base. Sepal quantity: Five. Sepal shape: Narrowly lanceolate. Length: About 2 mm. Diameter: About 0.5 mm. Sepal apex: Acute. Sepal margin: Entire. Color, both surfaces: 138A.

*Peduncle.*—Strength: Moderate. Angle: About 70° from vertical. Length: About 1 cm. Diameter: About 1 mm. Color: 141C.

*Reproductive organs.*—Stamens: Stamen quantity: Two. Anther shape: Roughly reniform. Anther length: About 1 mm. Anther color: 16B. Pollen amount: Scarce. Pollen color: 16B. Pistils: Pistil quantity: One. Pistil length: About 1 mm. Stigma shape: Conical. Stigma color: 16B. Style color: 16B. Ovary color: 16B.

*Seed.*—Seed production has not been observed.

Disease resistance: Plants of the new Sutera have not been noted to be resistant to Bacterial Crown Rot.

Temperature tolerance: Plants of the new Sutera have been observed to tolerant to temperatures from 0 to 40° C.

It is claimed:

1. A new and distinct cultivar of Sutera plant named 'Everwhite', as illustrated and described.

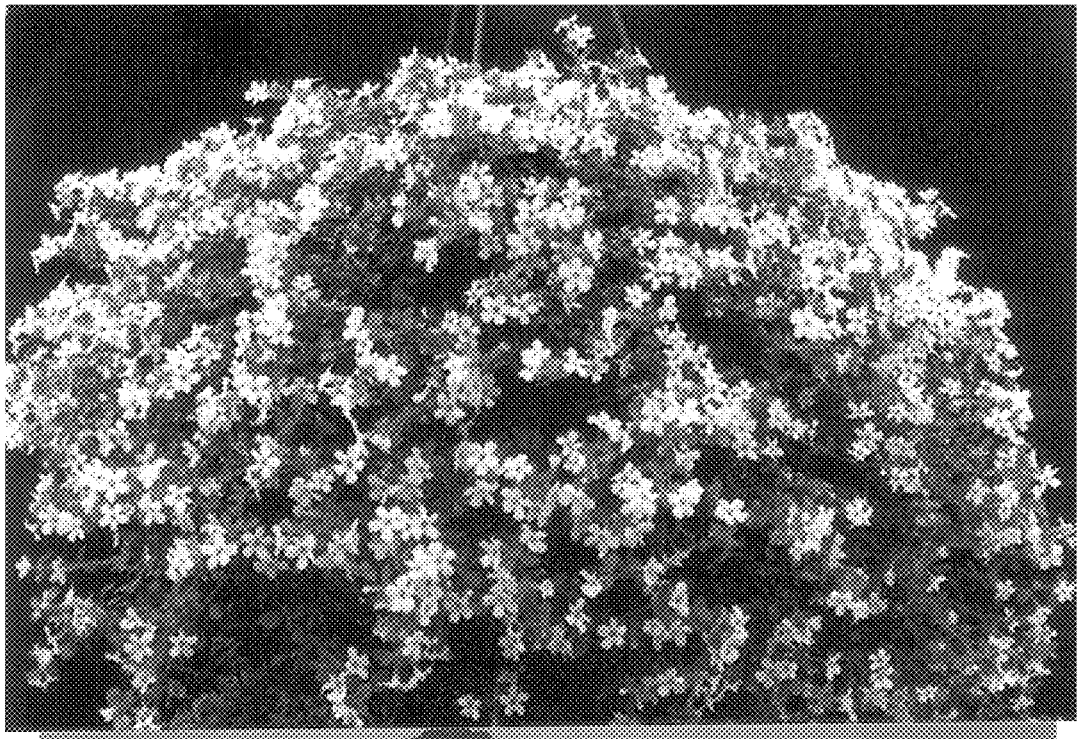
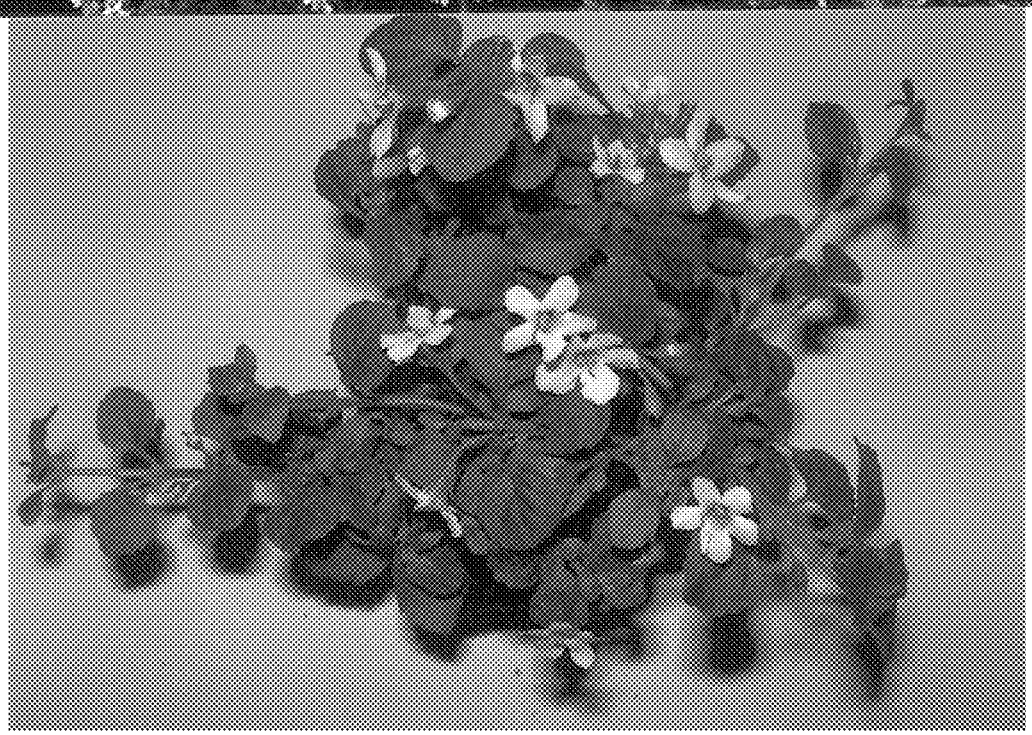

* * * * *